(12) United States Patent
Yoon et al.

(10) Patent No.: US 10,517,525 B2
(45) Date of Patent: Dec. 31, 2019

(54) SMART DIAGNOSTIC MOUTH GUARD SYSTEM

(71) Applicant: University of Florida Research Foundation, Inc., Gainesville, FL (US)

(72) Inventors: Yong-Kyu Yoon, Gainesville, FL (US); Xiaoyu Cheng, Gainesville, FL (US); Gloria Jung-a Kim, Gainesville, FL (US); Fong Wong, Ocala, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 14/760,641

(22) PCT Filed: Jan. 14, 2014

(86) PCT No.: PCT/US2014/011409
§ 371 (c)(1),
(2) Date: Jul. 13, 2015

(87) PCT Pub. No.: WO2014/110548
PCT Pub. Date: Jul. 17, 2014

(65) Prior Publication Data
US 2015/0305671 A1  Oct. 29, 2015

Related U.S. Application Data

(60) Provisional application No. 61/752,142, filed on Jan. 14, 2013.

(51) Int. Cl.
*A61B 5/00* (2006.01)
*A61B 5/01* (2006.01)
(Continued)

(52) U.S. Cl.
CPC .......... *A61B 5/4557* (2013.01); *A61B 5/0008* (2013.01); *A61B 5/01* (2013.01);
(Continued)

(58) Field of Classification Search
CPC ......... A61C 19/04; A61C 5/14; A61B 5/4557; A61B 5/0008; A61B 5/01
(Continued)

(56) References Cited

U.S. PATENT DOCUMENTS 5,078,153 A   1/1992  Nordlander
5,954,673 A * 9/1999  Staehlin ............... A61B 5/4205
                                                        433/68

(Continued)

FOREIGN PATENT DOCUMENTS

EP         1245197      10/2002
WO       2005/115225   12/2005
(Continued)

OTHER PUBLICATIONS

International Search Report for PCT/US2014/011409 dated May 13, 2014.
(Continued)

*Primary Examiner* — Scott Luan
(74) *Attorney, Agent, or Firm* — Thomas Horstemeyer, LLP

(57) ABSTRACT

Various examples are provided for a smart mouth guard for diagnosis, quantification, and/or management of e.g., bruxism. In one example, among others, a diagnostic mouth guard includes a plurality of pressure sensors and processing circuitry configured to provide pressure sensor data to an external processing unit when located in an oral cavity. The diagnostic mouth guard may also include temperature, pH and/or inertia sensors. In another example, a system includes the diagnostic mouth guard and the external processing unit (Continued)

such as, e.g., a smart phone, table or computer. The diagnostic mouth guard can communicate with the external processing unit over a wireless channel.

21 Claims, 10 Drawing Sheets

(51) Int. Cl.
    *A61M 21/02*     (2006.01)
    *A61F 5/56*     (2006.01)
    *A61B 5/22*     (2006.01)
    *A61M 21/00*     (2006.01)

(52) U.S. Cl.
    CPC .............. *A61B 5/228* (2013.01); *A61B 5/486* (2013.01); *A61B 5/4836* (2013.01); *A61B 5/4839* (2013.01); *A61B 5/681* (2013.01); *A61B 5/682* (2013.01); *A61B 5/6898* (2013.01); *A61B 5/7282* (2013.01); *A61B 5/742* (2013.01); *A61B 5/7455* (2013.01); *A61B 5/7475* (2013.01); *A61F 5/566* (2013.01); *A61M 21/02* (2013.01); *A61B 2562/0219* (2013.01); *A61F 2005/563* (2013.01); *A61M 2021/0027* (2013.01); *A61M 2205/3303* (2013.01)

(58) Field of Classification Search
    USPC ............. 600/301, 26, 27, 28, 24; 400/27, 31
    See application file for complete search history.

(56) References Cited

U.S. PATENT DOCUMENTS

| | | | |
|---|---|---|---|
| 6,089,864 A * | 7/2000 | Buckner | A61F 5/56 433/6 |
| 6,122,961 A | 9/2000 | Geen et al. | |
| 6,638,241 B2 | 10/2003 | Yerushalmy | |
| 6,941,952 B1 | 9/2005 | Rush, III | |
| 2002/0094509 A1 * | 7/2002 | Durbin | A61C 9/00 433/213 |
| 2004/0158194 A1 | 8/2004 | Wolff et al. | |
| 2005/0113654 A1 | 5/2005 | Weber et al. | |
| 2006/0166157 A1 | 7/2006 | Rahman | |
| 2006/0210951 A1 | 9/2006 | Levanoni et al. | |
| 2006/0271199 A1 | 11/2006 | Johnson | |
| 2007/0106138 A1 | 5/2007 | Beiski et al. | |
| 2009/0210032 A1 | 8/2009 | Beiski et al. | |
| 2009/0220563 A1 | 9/2009 | Shachar | |
| 2011/0066066 A1 | 3/2011 | Van Kemenade et al. | |
| 2011/0184319 A1 | 7/2011 | Mack et al. | |
| 2011/0184663 A1 | 7/2011 | Mack et al. | |
| 2012/0123225 A1 | 5/2012 | Al-Tawil | |
| 2012/0172679 A1 * | 7/2012 | Logan | A61B 5/082 600/301 |
| 2013/0066236 A1 | 3/2013 | Herman et al. | |
| 2013/0211270 A1 | 8/2013 | St Laurent et al. | |
| 2014/0187875 A1 | 7/2014 | Paris et al. | |
| 2014/0188010 A1 | 7/2014 | Paris et al. | |
| 2014/0248574 A1 | 9/2014 | Yoon et al. | |

FOREIGN PATENT DOCUMENTS

| | | |
|---|---|---|
| WO | 2008061328 A2 | 5/2008 |
| WO | 2016/183442 | 11/2016 |

OTHER PUBLICATIONS

Jules Kieser, et al., "Measuring Intraoral Pressure: Adaptation of a Dental Appliance Allows Measurement During Function"?, Dysphagia, vol. 23, No. 3, pp. 237-243, 2008.

Takahashi S, Ono T, Ishiwata Y, and Kuroda T., "Effect of changes in the breathing mode and body position on tongue pressure with respiratory related oscillations"?, Am J. Orthod Dentofacial Orthop., vol. 115, No. 3, pp. 239-246, Mar. 1999.

K. Ahlberg, et al., "Bruxism and sleep efficiency measured at home with wireless devices"?, Journal of Oral Rehabilitation, vol. 35, pp. 567-571, 2008.

Jungho Kim, et al."Development of wireless bruxism monitoring device based on pressure sensitive polymer composite", Sensors and Actuators A, vol. 163, pp. 486-492, 2010.

J. Clauss, M. Sattler, W.D. Seeher and B. Wolf, "In-vivo monitoring of bruxism with an intelligent tooth splint—Reliability and validity"?, IFMBE Proceedings, vol. 25, No. 11, pp. 108-111, Sep. 2009.

Mart A.; Barrientos, A..; Lafont, P.; Colorado, J.; Castedo, P.L.; Gonz, R.; , "Polymeric piezoelectric sensors and remote communication for detection of bruxism," Industrial Technology (ICIT), 2010 IEEE International Conference on , pp. 268-273, Mar. 14-17, 2010.

Alvarez, A.; Barrientos, A.; Lantada, A.; Morgado, P.; Cepeda, P.; Herranz, R.; "Diagnosis of Bruxism Based on Polymeric Piezoelectric Sensors and Remote Communication"?, [Online]. Available: http://www.disam.upm.es/.

Andres Diaz Lantada, Handbook of Active Materials for Medical Devices: Advances and Applications, Pan Stanford Publishing, Singapore, 2012, pp. 199-207.

H. Takeuchi, et al. "A piezoelectric film based intra-splint detection method for bruxism"?, The Journal of Prosthetic Dentistry, vol. 86, issue 2, pp. 195-202, Aug. 2001.

Gonzalez, C.; Lantada, A., "A wearable passive force sensor powered by an active interrogator intended for intra-splint use for the detection and recording of bruxism," Pervasive Computing Technologies for Healthcare, 2009. PervasiveHealth 2009. 3rd International Conference on , pp. 1-4, Apr. 1-3, 2009.

Jung Ho Kim; McAuliffe, P.; O'Connel, B.; Diamond, D.; King Tong Lau; , "Development of Bite Guard for Wireless Monitoring of Bruxism Using Pressure-Sensitive Polymer," Body Sensor Networks (BSN), 2010 International Conference on , pp. 109-116, Jun. 7-9, 2010.

M.C. Raadsheer, et al., Contribution of Jaw Muscle Size and Craniofacial Morphology to Human Bite Force Magnitude, Journal of Dental Research, vol. 78, No. 1, pp. 31-42, Jan. 1999.

No Author, mHealth New Horizons for Health Through Mobile Technologies, Global Observatory for eHealth Series, vol. 3, World Health Organization (Jun. 20, 2011).

Igarashi, Yoshimasa. Analysis of the Denture Dynamics in RPD's. 1989 Journal of Japanese Prosthdont Society, 33:369-375.

Agard, Kathleen, et al. "Mouth guard for treating bruxism with electrostimulation." University of Wiconsin. Madison (Dec. 2001).

Humphries, Courtney. "Mouthpieces Gather Impact Data from Football Players", Mouthpieces Gather Impact Data from Football Players—MIT Technology Review (Oct. 2011). https://www.technologyreview.com/s/425724/mouthpieces-gather-impact-data-from-football-players/.

BiteStrip, up2dent, http://www.pxt.pt:8080/bitestripweb/FMPro?-DB=BS_SS_CMS.fp5&-Format=bs_insert.html&-Max=1&bsss=bs&sprache=au&seitenid=home&-Find.

* cited by examiner

SMART DIAGNOSTIC MOUTH GUARD SYSTEM

CROSS REFERENCE TO RELATED APPLICATIONS

This application is the 35 U.S.C. § 371 national stage application of PCT Application No. PCT/US2014/011409, filed Jan. 14, 2014, which claims priority to and the benefit of co-pending U.S. provisional application entitled "SMART DIAGNOSTIC MOUTH GUARD SYSTEM" having Ser. No. 61/752,142, filed Jan. 14, 2013, which is hereby incorporated by reference in its entirety.

BACKGROUND

Chronic stress is a major cause of chronic illness, which in turn is a major driver of escalating health care costs in the US. Many Americans are living with moderate or high levels of stress. Since assessment of chronic stress depends almost exclusively on retrospective self-reporting, underreporting poses a serious impediment to clinical assessment, early intervention, and primary prevention. Among the many symptoms and pathological consequences of stress, nocturnal bruxism has drawn attention from many clinicians in related fields.

Bruxism is characterized by the grinding of the teeth and typically includes the clenching of the jaw. Bruxism normally occurs during sleep and can result in a variety of health issues. The etiology of bruxism is unclear and varied, but it has been known to manifest in tooth wear, signs and symptoms of temporomandibular disorders (TMD), headaches, toothache, mobile teeth, and various problems with dental restorations as well as with fixed and removable prostheses. Dentists have relied on polysomnography and various versions of electromyography (EMG) to ascertain, diagnose, approximate the extent of, and reduce nocturnal bruxism.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
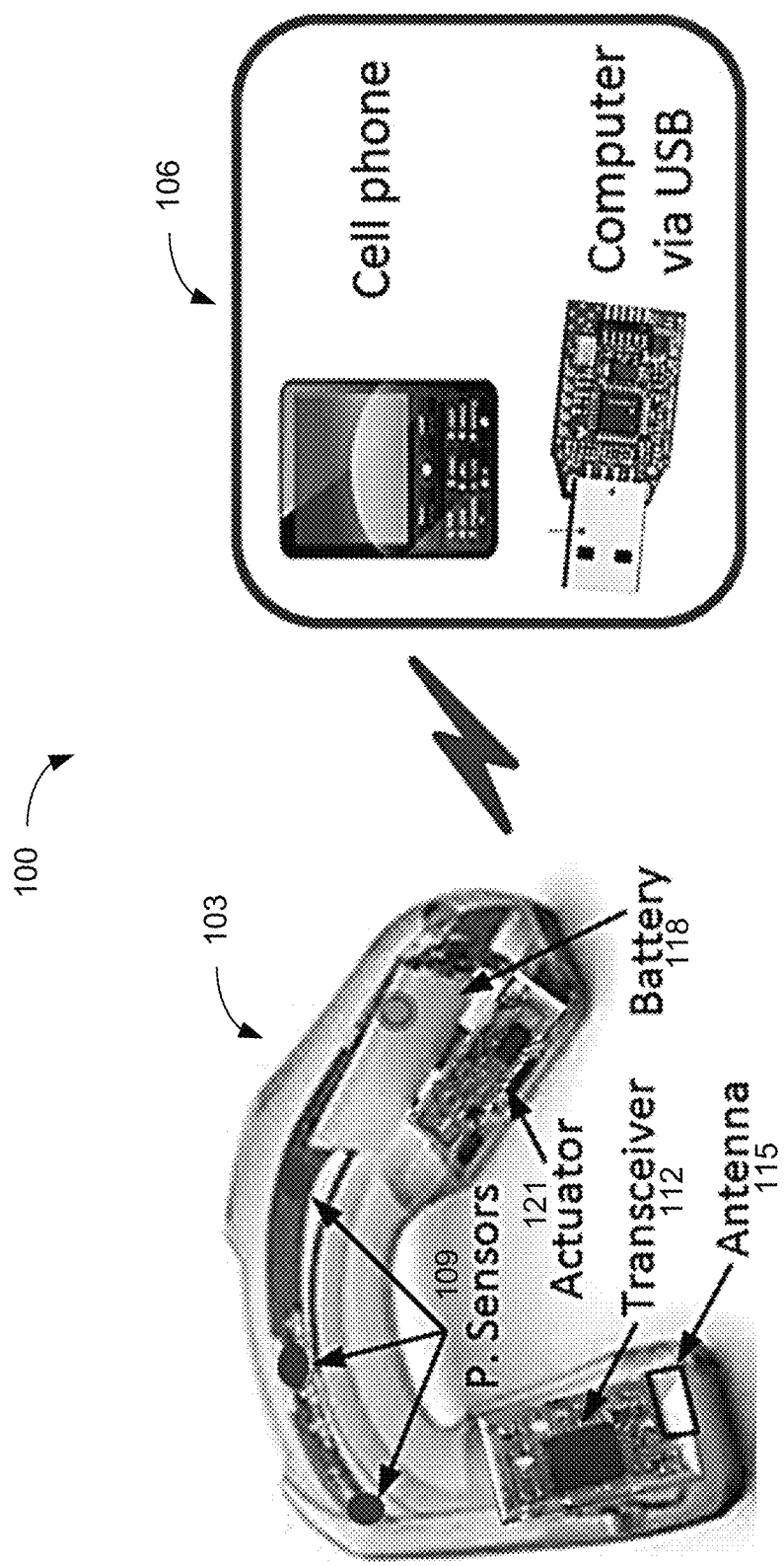
FIG. 1 is an example of a smart mouth guard system (SMS) in accordance with various embodiments of the present disclosure.

Disclosed herein are various embodiments of related to a smart mouth guard for diagnosis, quantification, and/or management of, e.g., bruxism. Reference will now be made in detail to the description of the embodiments as illustrated in the drawings, wherein like reference numbers indicate like parts throughout the several views.

People bite, grind or clench their teeth for non-functional purposes throughout a day. This can happen to people of nearly all ages with an exerted biting force that can range from about 10 lbs. to about 200 lbs. Bruxism includes the activities of grinding or clenching the teeth and may result in excessive wear of the jaw joints, muscles and teeth, headache, depression, muscle soreness, and/or temporomandibular disorder.

A smart mouth guard system (SMS) capable of diagnosis, quantification, and management may be used in the identification and control of bruxism. The SMS provides the ability to measure human biting and clenching force in real-time and wirelessly transmit data form the mouth guard to an external processing unit such as, e.g., a personal computer, tablet, smart phone, smart watch, etc. Referring to FIG. 1, shown is an example of a SMS 100 including a mouth guard 103 (e.g., an occlusal splint) and an external processing unit 106 such as, e.g., a cell phone or a computer. The mouth guard 103 may include an array of capacitive pressure sensors 109, a wireless transceiver 112, an antenna 115, and a wireless power delivery/management system for the battery 118. In addition, the system may be equipped to monitor conditions of the oral environment, such as pH and temperature using appropriate sensors. Inertia sensors such as, e.g., accelerometers and/or gyroscopes may also be included in the mouth guard 103 to monitor motion and/or orientation of the wearer. An actuator 121 may be included that controls charging of and data acquisition from the pressure sensors 109 and/or other sensors of the mouth guard 103. The SMS 100 can utilize wireless telemetry such as, e.g., Bluetooth or near-field communication capabilities to communicate with the external processing unit 103 and/or a USB transceiver dongle which can be connected to, e.g., a personal computer or tablet. Applications (apps) or other programs executed by the external processing unit 106 can control communications between the mouth guard 103 and external processing unit 106 and/or data management. The SMS can simplify self-monitoring, provide customized feedback, and intervene—either automatically prompt a clinician to intervene in person or through the apps executing on the external processing unit 106.

Figure 2A:
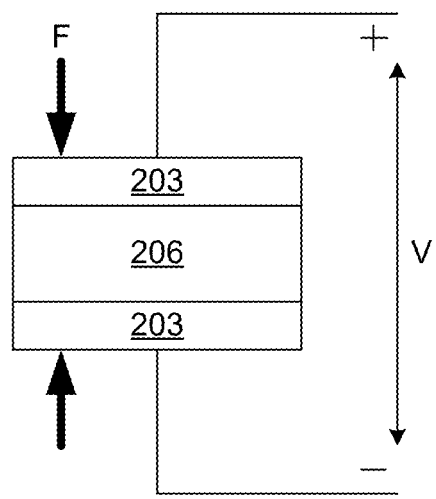
FIGS. 2A and 2B are examples of capacitive pressure sensors in accordance with various embodiments of the present disclosure.

The capacitive pressure sensors 109 utilize capacitive based transducers that are incorporated into the mouth guard 103. Capacitive based transducers can provide good tactile or distance, strain, humidity, gas, pressure, and/or biomedical sensing. FIG. 2A illustrates an example of a floating sensor including two conductive pads 203 separated by an elastic material (or elastomer) 206. Force (F) applied to one or both of the conductive pads 203 compresses the elastic material 206 and changes the capacitance of the sensor 109. Knowing the characteristics of the elastic material 206 allows the capacitance of the pressure sensor 109 to be correlated to the applied force (F). The capacitance of the sensor 109 may be detected based on the voltage (V) between the conductive pads 203. A grounded sensor including a single conductive pad 203 may be used in a similar fashion.

Capacitance may be defined as:

$$C \triangleq \frac{q}{V}$$

and the two-dimensional (2D) surface charge density on a metal pad surface may be given by:

$$\rho_s = \frac{q}{A}.$$

From Gauss's Law, the charge is given by:

$$q = \oiint_S D \cdot dA.$$

Using Maxwell's equation:

$$D = \varepsilon E$$

we have:

$$E = \frac{q}{4\pi \varepsilon r^2},$$

where $\varepsilon$ is the permittivity. By substituting $\rho_S$ into the equation, we obtain:

$$E = \frac{\rho_s A}{4\pi \varepsilon r^2} = \frac{\rho_s}{\varepsilon} = \frac{q}{\varepsilon A}.$$

Since:

$$V = -\int_0^t E \, dl = Et$$

then:

$$V = Et = \frac{qt}{\varepsilon A} \text{ and } C = \frac{q}{V} = \frac{\varepsilon A}{t}$$

which is identical to the floating configuration.

Figure 2B:
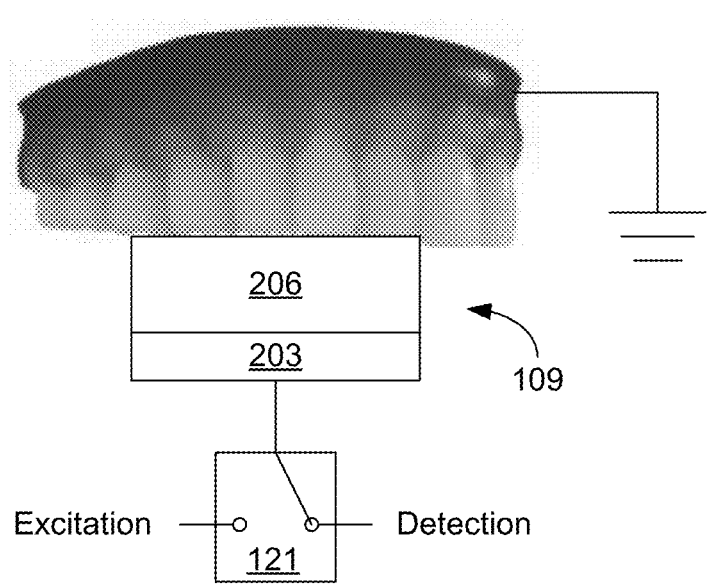

FIG. 2B illustrates an example of a grounded sensor including a single conductive pad 203. In the example of FIG. 2B, the second conductive plate is provided by the mouth of a user wearing the mouth guard 103, which is grounded. The elastic material 206 is biocompatible for use by the user. When the user bites down on the elastic material 206, the capacitance of the pressure sensor varies with the applied pressure. Actuator 121 allows for charging of the conductive pad 203, followed by detection of the plate voltage variation.

Figure 3:
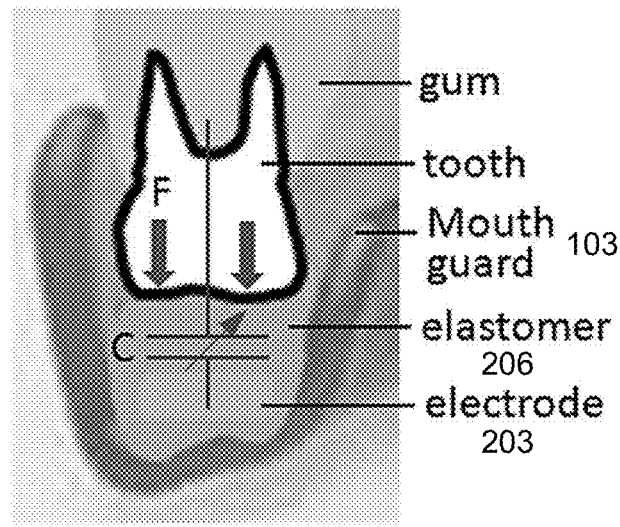
FIG. 3 is a graphical representation of a cross-sectional view illustrating capacitive pressure sensing by the mouth guard of the SMS of FIG. 1 in accordance with various embodiments of the present disclosure.

Referring to FIG. 3, shown is a graphical representation of a cross-sectional view illustrating capacitive pressure sensing by the mouth guard 103 in accordance with various embodiments of the present disclosure. Included in the mouth guard 103 is a grounded sensor including a single conductive pad (or electrode) 203. The oral tissue (gum) and tooth serve as a counter electrode and an elastic polymeric material 206 (or elastomer such as, e.g., polydimethylsiloxane (PDMS), polymethylmethacrylate (PMMA), or a combination thereof) serves as a dielectric layer for the capacitor. Typical chewing pressure is in the range of about 10 lbs to about 200 lbs (about 100 kPa to about 2000 kPa). In order to address the bruxing pressure level, both silicone (polydimethysiloxane: PDMS) with a thickness in the range of about 100 μm to about 500 μm and acrylic (polymethylmethacrylate: PMMA) with a thickness of about 100 μm to about 500 μm may be used, where the Young's modulus of PDMS and PMMA is 360 kPa and about 1800 kPa to about 3100 kPa, respectively. Both materials are biocompatible and are routinely used in restorative dentistry.

When a user bits down and/or grinds teeth (e.g., when bruxing occurs), the tooth exerts pressure on the elastomer material 206 underneath the tooth, changing the gap between the tooth and the electrode or conductive pad 203, resulting in a capacitance change. The capacitance change is proportional to the applied pressure and thus the bruxing level. By monitoring the capacitance change, it is possible to quantify the extent and severity of bruxism.

Figure 4A:
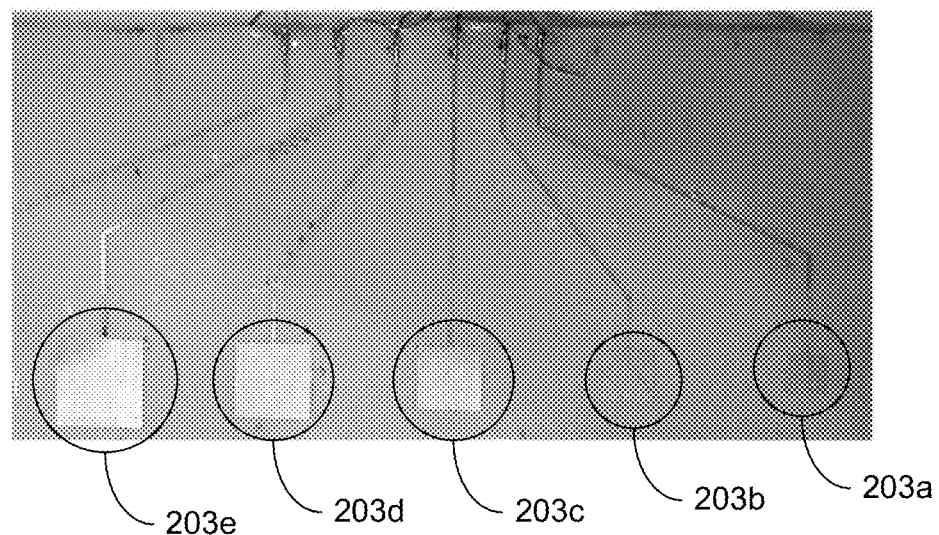
FIGS. 4A and 4B show example of conductive pads on a flexible substrate that may be used for capacitive pressure sensors in the SMS of FIG. 1 in accordance with various embodiments of the present disclosure.

Capacitive pressure sensors 109 may be fabricated using a flexible printed circuit board including a flexible substrate (e.g., RO3003 by Rogers Inc.). FIG. 4A shows an image of the conductive (or metallic sensing) pads 203 on the flexible substrate with a PDMS layer providing the elastic material 206. The conductive pads 203 were patterned using a milling machine (e.g., S100 by LPKF Inc.) on a flexible substrate with a thickness of, e.g., 10 mil. Other substrate thicknesses may be used such as, e.g., about 1 mil to about 100 mil. The sensitivity of the capacitive pressure sensors 109 can vary with pad size, so different sizes were fabricated. The dimensions of the conductive pads 203 from right to left are 3 mm×3 mm (203a), 4 mm×4 mm (203b), 5 mm×5 mm (203c), 6 mm×6 mm (203d), and 7 mm×7 mm (203e). The elastic material 206 can then be applied over the fabricated conductive pads 203. For example, a kit from Dow Corning may be used to apply a silicon elastomer coating of PDMS.

Figure 4B:
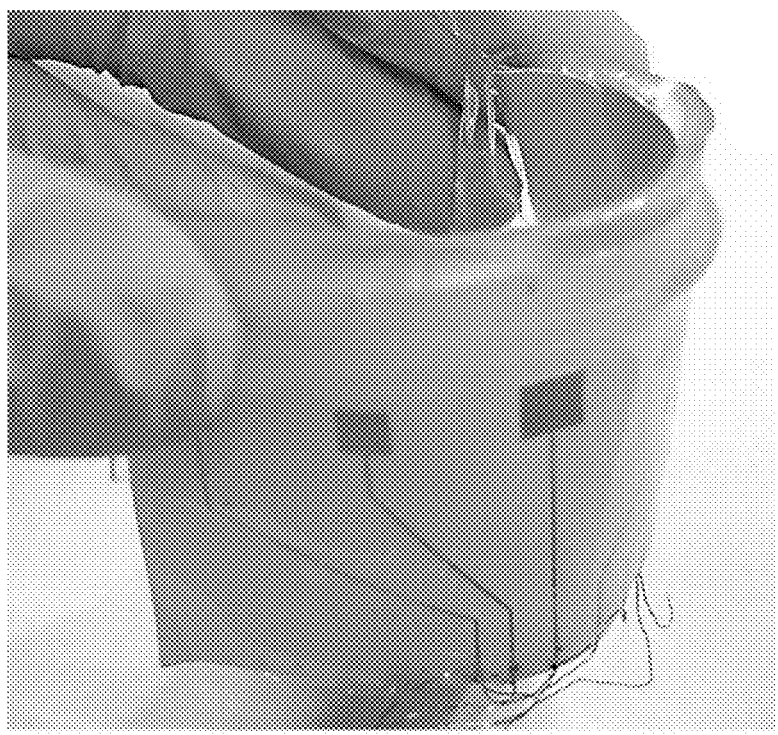

FIG. 4A shows the conductive pads 203 on the flexible substrate and PDMS layer lying flat. Since both the thin substrate and PDMS layer are flexible, the capacitive pad sensor 109 is deformable and can be fit in the uneven trench of the mouth guard 103. FIG. 4B shows an image of the conductive pads 203 on the flexible substrate and PDMS layer in a bent position. This flexibility makes the mouth guard 103 comfortable to wear.

Figure 5A:
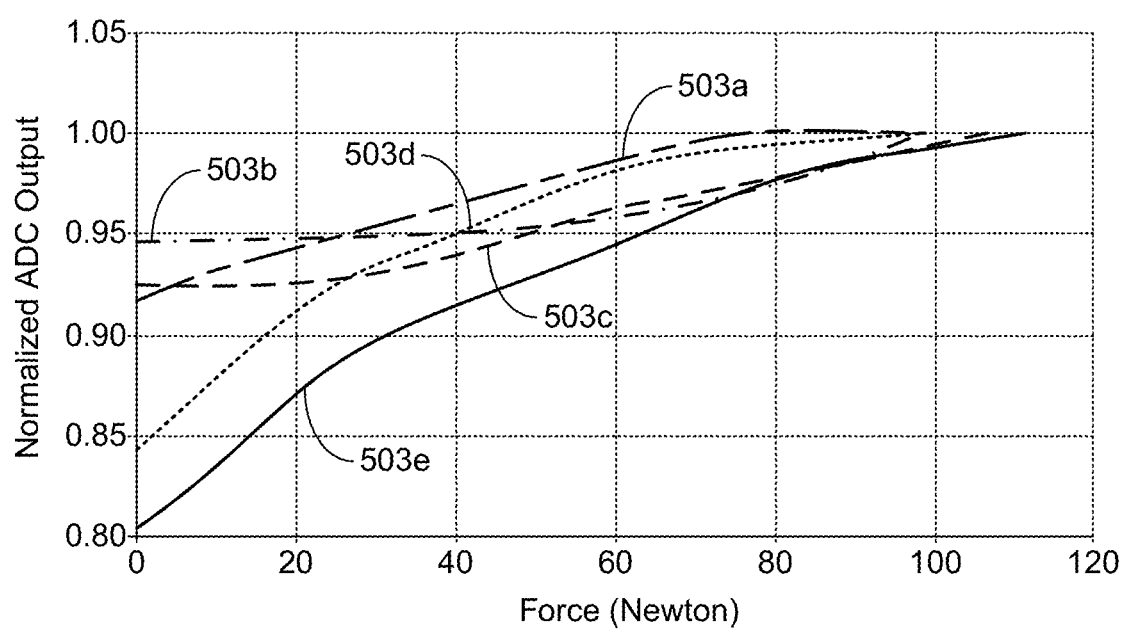
FIGS. 5A and 5B are plots illustrating the effect of pad size and elastic material thickness on the capacitive pressure sensors of FIG. 1 in accordance with various embodiments of the present disclosure.
Figure 5B:
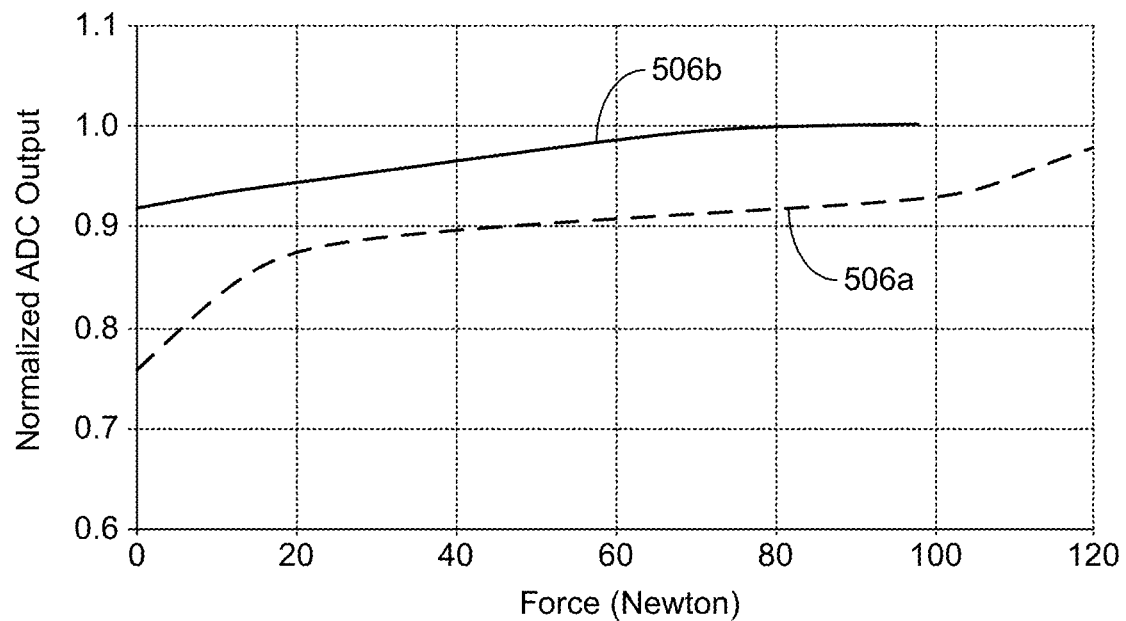

The effect of the different conductive pad sizes is illustrated in FIG. 5A. The output of the conductive pads 203 was connected to an analog-to-digital converter (ADC) to digitize the data. FIG. 5A depicts the plots of the normalized ADC output with respect to the applied force for each conductive pad size: curve 503a for the 3 mm×3 mm pad 203a, curve 503b for the 4 mm×4 mm pad 203b, curve 503c for the 5 mm×5 mm pad 203c, curve 503d for the 6 mm×6 mm pad 203d, and curve 503e for the 7 mm×7 mm pad 203e. As can be seen, the larger pad sizes exhibit a wider ADC output range. The effect of the thickness of the elastic material 206 was also examined. FIG. 5B depicts the plots of the normalized ADC output with respect to the applied force for two different thicknesses of the PDMS layer: curve 506a for 3 mm and curve 503b for 4.5 mm.

Figure 6A:
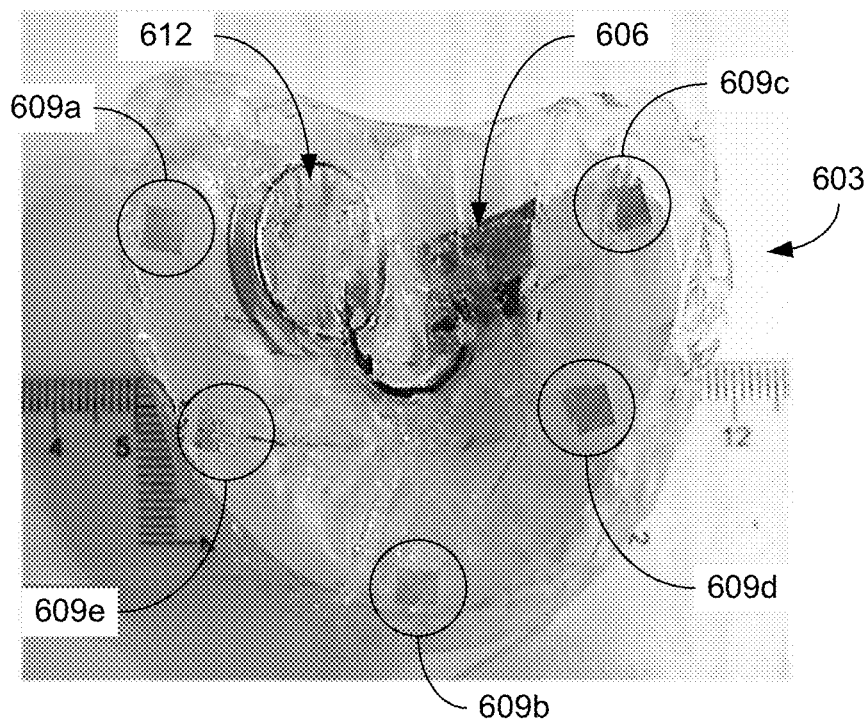
FIGS. 6A-6D are images of an example of a mouth guard of the SMS of FIG. 1 in accordance with various embodiments of the present disclosure.
Figure 6B:
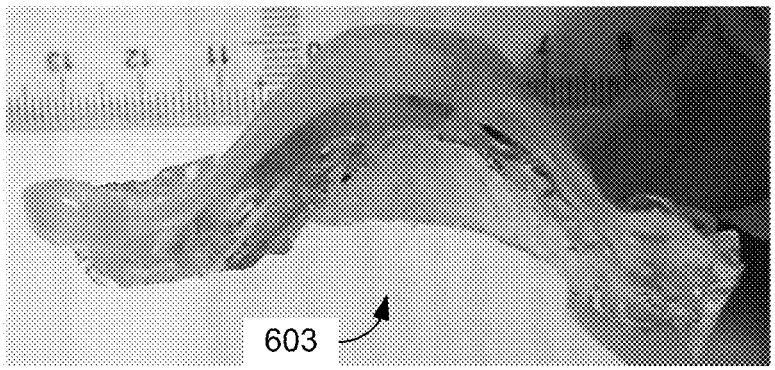
Figure 6C:
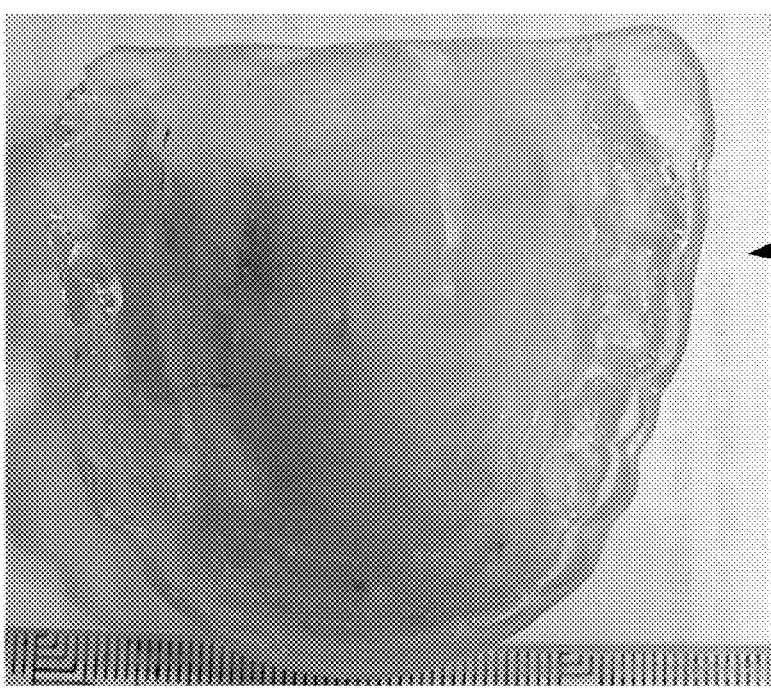
Figure 6D:
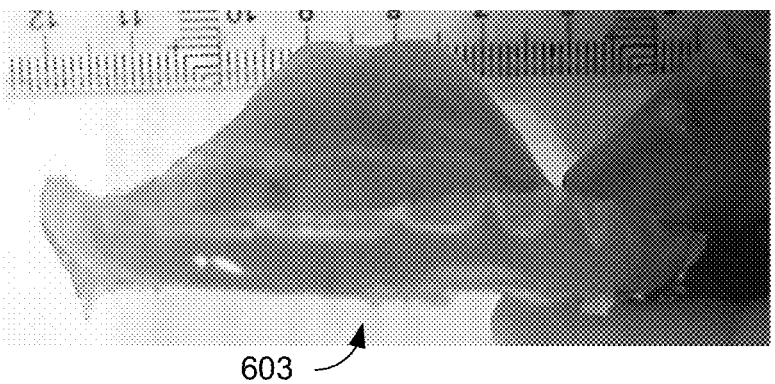

Referring next to FIGS. 6A-6D, shown are images of an example of a mouth guard 603 in accordance with various embodiments of the present disclosure. The mouth guard 603 of FIG. 6A includes five capacitive pressure sensors 609 (5 mm×5 mm) distributed along a palatal surface of the mouth guard 603. Other sensors such as, e.g., a temperature sensor and/or an inertia sensor may also be included. For example, one or more accelerometers and/or gyroscopes may be integrated into the mouth guard 603 to provide information regarding movement of the mouth guard 103 and/or the wearer. For instance, MEMS accelerometers and/or gyroscopes can provide six-axis information regarding, e.g., movement, tilt or shock. The mouth guard 603 also includes electronic processing circuitry 606 for sensing and/or wireless communications, and a power source 612 such as, e.g., a button cell battery. The capacitive pressure sensors 609, electronic processing circuitry 606 and power source 612 were implemented on a flexible substrate and encased in PDMS using a professional dental molding process. Temperature, pH and inertia sensors may also be implemented on the flexible substrate and encased in PDMS. The mouth guard 603 was fitted to a user's upper teeth and palate for testing. The backside metal of the flexible substrate provides shielding of electrical noises from the human body. FIGS. 6B, 6C, and 6D are images of the back, top, and front views of the mouth guard 603, respectively.

Figure 7:
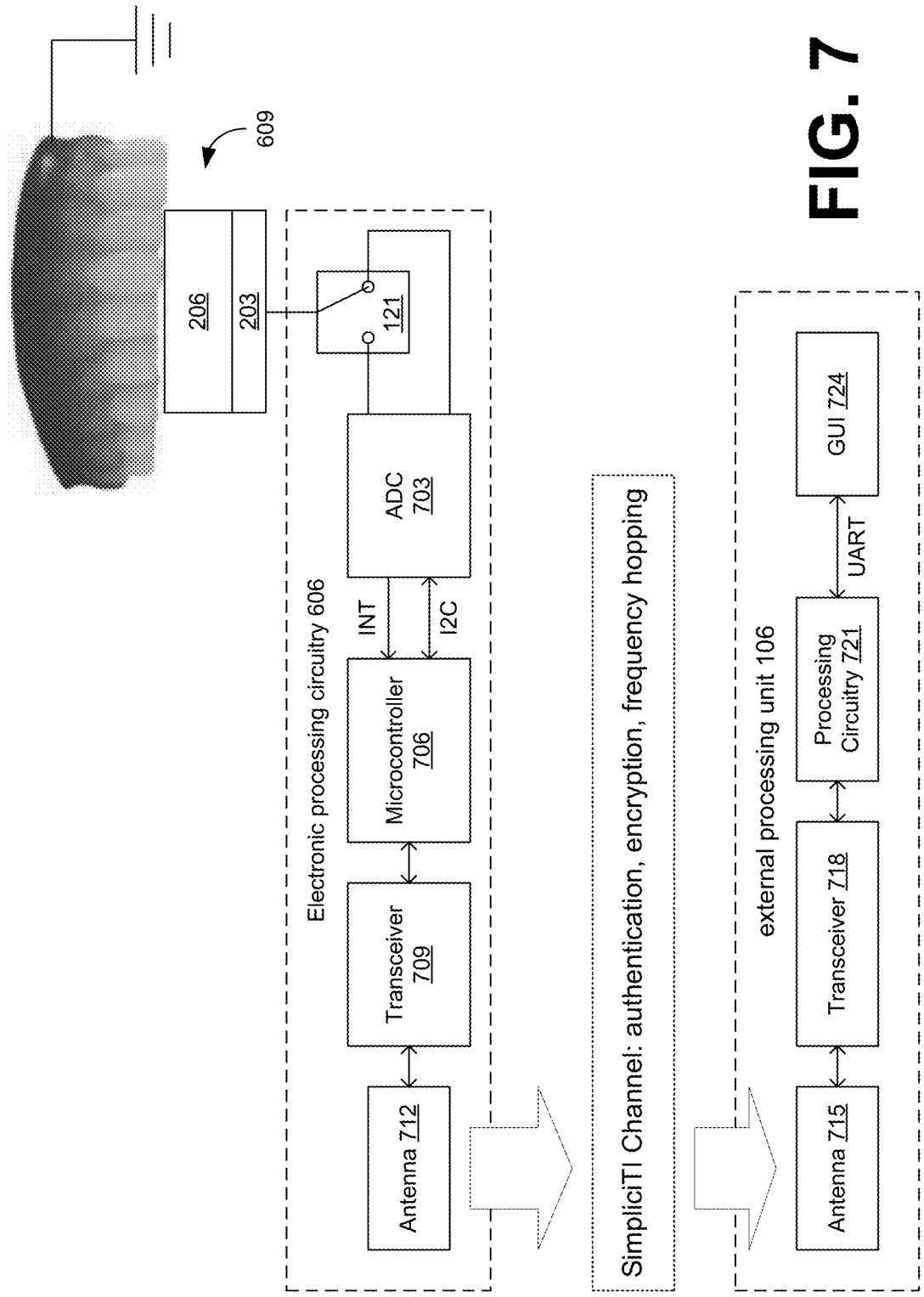
FIG. 7 is a graphical representation of an example of the SMS of FIG. 1 in accordance with various embodiments of the present disclosure.

The electronic processing circuitry 606 for sensing and/or wireless communications includes a transceiver, a microcontroller, one or more ADCs, and passive radio frequency (RF) components such as, e.g., an antenna, transmission lines, and a balun. Referring to FIG. 7, shown is a graphical representation of an example of the SMS including, e.g., mouth guard 600 of FIGS. 6A-6D or mouth guard 103 of FIG. 1. For example, each capacitive pressure sensor 609 may be coupled to an ADC 703 (e.g., an AD7746 from Analog Device) to digitize the output data, which is then relayed for processing by a microcontroller 706. The microcontroller 706 can provide the acquired sensor data to an external processing unit 106 through a transceiver 709 and antenna 712. The microcontroller 706 and transceiver 709 may be implemented together as a microcontroller unit (MCU) such as, e.g., a CC2510 system on a chip (SoC) by Texas Instruments Inc., which includes a microcontroller and transceiver for more compact and power efficient system implementation. In some implementations, the electronic processing circuitry 606 may include memory to store sensor data for subsequent transmission to the external processing unit 106 and/or code or instructions that may be executed by the microcontroller 706.

Figure 8A:
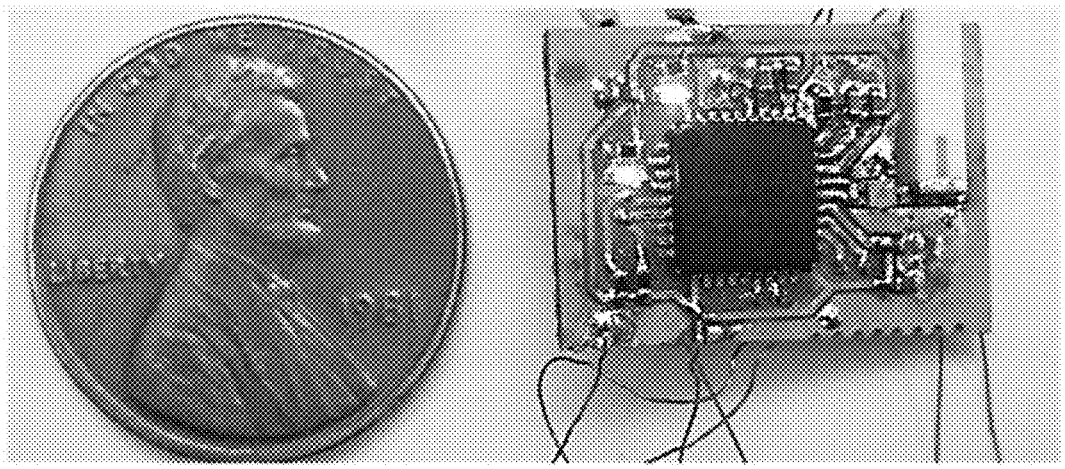
FIGS. 8A and 8B are images of an example of electronic processing circuitry of the SMS mouth guard of FIG. 7 in accordance with various embodiments of the present disclosure.
Figure 8B:
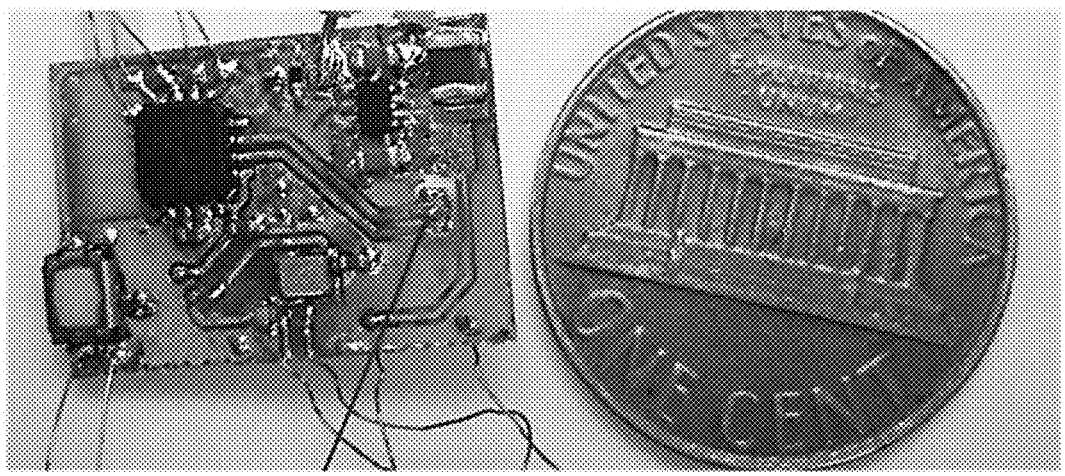

FIGS. 8A and 8B show front and back views of an implementation of the electronic processing circuitry 606. The electronic processing circuitry 606 was fabricated on a flexible substrate (e.g., RO 3003, Rogers, Inc.) with a dimension of approximately 15 mm×15 mm. A temperature sensor in the chip of ADC 703 (e.g., CC1100, Texas Instruments Co.) may be used to provide an indication of whether a user is wearing the mouth guard, e.g., to address compliance issues. Real-time temperature changes with a resolution of 0.1° C. and an accuracy of ±0.1° C. could be detected. The CC2510 chip contains an enhanced 8051 core microprocessor as well as an ISM band transceiver. Between the CC1100 ADC 703 and the CC2510 microcontroller 706/transceiver 709, an I2C communication protocol may be used. The digitized pressure information is modulated in the CC2510 microcontroller 706 and then transmitted to the free space wireless channel (or link) via a chip antenna 712. Acceleration and/or gyroscopic sensors in a chip (not shown) may also be in communication with microcontroller 706 to provide indications of movement. In some implementations, at least a portion of the electronic processing circuitry 606 may be turned on and off using a magnetic reed switch. While the example of FIGS. 8A and 8B uses chip components for the concept proof, the circuit may be implemented using customized VLSI circuits. The whole electronic circuit and sensors may be realized in a size scale of a few millimeters or micrometers.

Power for the electronic processing circuitry 606 may be provided by a power source such as, e.g., a battery 118 (FIG. 1) or 612 (FIG. 6A). It may be desirable to avoid having to replace the battery. A wireless power delivery system may be used to supply power to a rechargeable battery through inductive coupling. The electronic processing circuitry 606 may be configured to regulate power delivery from an external source to recharge the battery. For example, a spirial antenna may be used for near field power coupling and bq500110 and bq51013 ICs from Texas Instruments may be used as the power transmitter and the receiver, respectively. Since the bq500110 and bq51013 ICs are highly integrated chips, nearly no peripherals are required on the receiver side for power collection, making it ideal for device size reduction.

Figure 9:
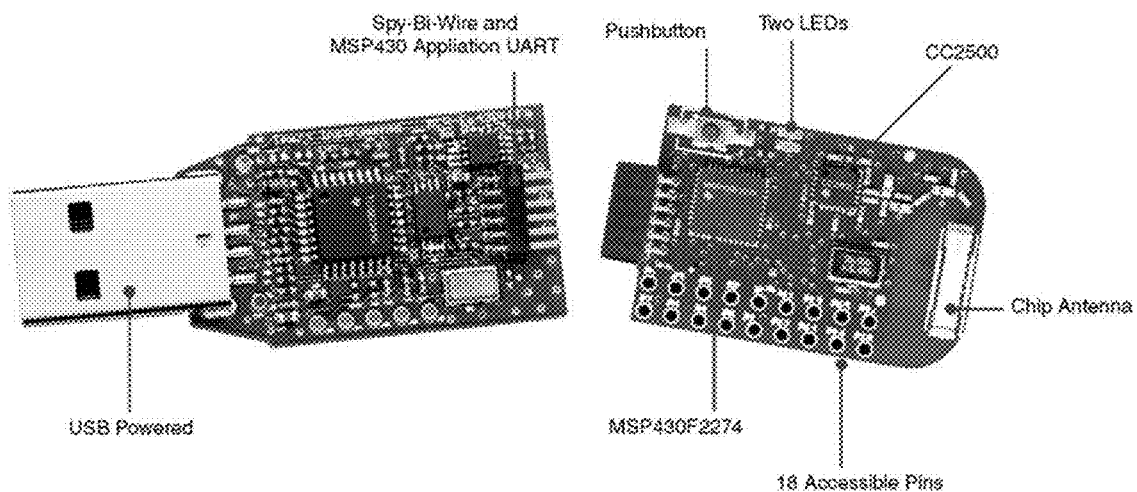
FIG. 9 is an example of a transceiver and antenna used in an external processing unit of the SMS of FIG. 1 in accordance with various embodiments of the present disclosure.

Referring back to FIG. 7, the external processing unit 106 includes an antenna 715 and transceiver 718 that receives the transmitted sensor information for analysis and processing by processing circuitry 721. The SMS can utilize wireless telemetry (e.g., a transceiver that interfaces with a computer though a USB port) for self-monitoring and self-management of chronic stress using nocturnal bruxism as a stress indicator. The signal is transmitted over a wireless channel (or link) through a chip antenna 712 and received by antenna 715 and transceiver 718. For example, a transceiver 718 and antenna 715 circuit including an MSP 430 IC and a CC2500 IC by Texas Instruments, Inc. may be provided in, e.g., a USB dongle shape as shown in FIG. 9. The transceiver/antenna circuit may be configured to be plugged into the external processing unit 106 such as, e.g., a computing device (or PC) through a USB connector. Transmission between the mouth guard and the external processing unit 106 may be over, e.g., a 2.4 GHz communication link, a 403-405 MHz medical implant communication service (MICS) band, or other industry science medicine (ISM) bands including, e.g., 433 MHz, 915 MHz, and 5.8 GHz.

Figure 10:
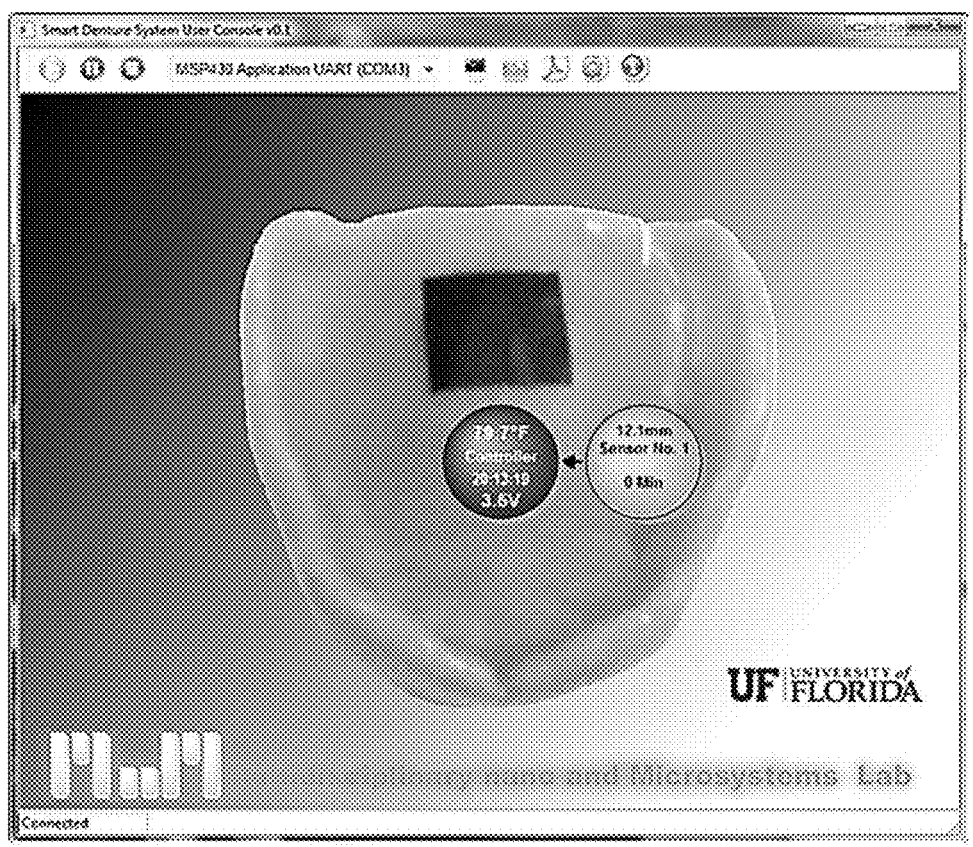
FIG. 10 is an example of a graphical user interface shown on a display (e.g., a computer screen or smart phone display) of the SMS of FIG. 1 in accordance with various embodiments of the present disclosure.

Communications between the mouth guard and external processing unit 106 may be carried out using a variety of communication protocols such as, e.g., SimpliciTI™ For instance, a SimpliciTI channel may be used for authentication, encryption, frequency hopping, etc. SimpliciTI™ is a simple communication protocol especially designed for low cost and small scale network. Since it contains a device switch to change between sleep and active states, it is also known as a low power consuming protocol. The signal is transferred to a processing circuitry 721, where it may be rendered and displayed on a screen or display via a graphical user interface (GUI) 724 such as illustrated in FIG. 10. The data may then be displayed in a Windows GUI operating within the Windows API. Both real time and statistic data may be made available to the user through the GUI 724. The GUI 724 may also allow the user to configure operation of the electronic processing circuitry 606 of the mouth guard.

In various embodiments, the processing circuitry 721 is implemented as at least a portion of a microprocessor. The processing circuitry 721 may be implemented using one or more circuits, one or more microprocessors, application specific integrated circuits, dedicated hardware, digital signal processors, microcomputers, central processing units, field programmable gate arrays, programmable logic devices, state machines, or any combination thereof. In yet other embodiments, the processing circuitry 721 may include one or more software modules executable within one or more processing circuits. The processing circuitry 721 may further include memory configured to store instructions and/or code that causes the processing circuitry to execute analysis and processing functions.

Figure 11A:
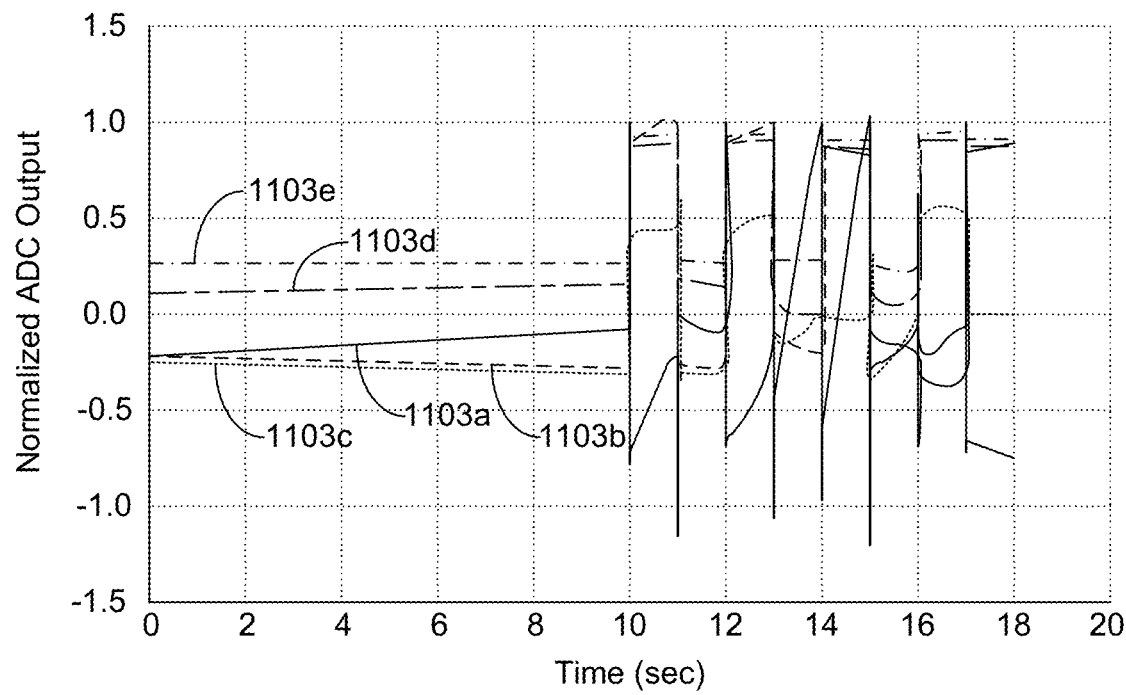
FIGS. 11A and 11B are plots of examples of pressure sensor data obtained by the SMS of FIG. 1 in accordance with various embodiments of the present disclosure.

Testing was performed by a user wearing the mouth guard of FIGS. 6A-6D in communication with an external processing unit 106 such as, e.g., a desktop personal computer. Operation was initially verified by recording a series of four bits. Data was collected by the SMS in real-time by the desktop personal computer. When active, data may be sampled for a predefined period such as, e.g., 0.1 sec, 0.5 sec, or 1 sec. The normalized ADC output curves 1103a-1103e are plotted in FIG. 11A for the five pressure sensors 609a-609e of FIG. 6A, respectively. The actuator 121 (FIG. 7) initiates sampling when pressure is applied and applies excitation when pressure is removed.

The electronic processing circuitry 606 may be programmed to maintain at least a portion of the circuitry in a sleep mode as long as the detected pressure level is below a predefined threshold. In this way, low pressure episodes are not recorded and data not transmitted. Once the detected pressure level exceeds the predefined threshold level, the electronic processing circuitry 606 switches to active mode to collect the pressure sensing data. When supra-threshold forces are present for a sufficiently long time, the force signal may be integrated over a specific time period. If the integral exceeds a threshold value, then the data may be stored in memory for later transmission or may be provided through real-time transmission. Since the average bruxing time per night is known to be approximately 10 minutes, use of a sleep mode may extend the system lifetime from one hour to six nights. In some implementations, multiple integrated data packets can be accumulated in memory before a batch transmission is initiated. For example, a brief transmission burst may be initiated for a few milliseconds for every minute during the active mode. Since the main power consumption in the SMS occurs during data transmission, batch data transmission can significantly reduce system power consumption. If the data transmission rate is reduced from 0.1 sec to 10 sec, the battery time may be extended by approximately 100 times.

Figure 11B:
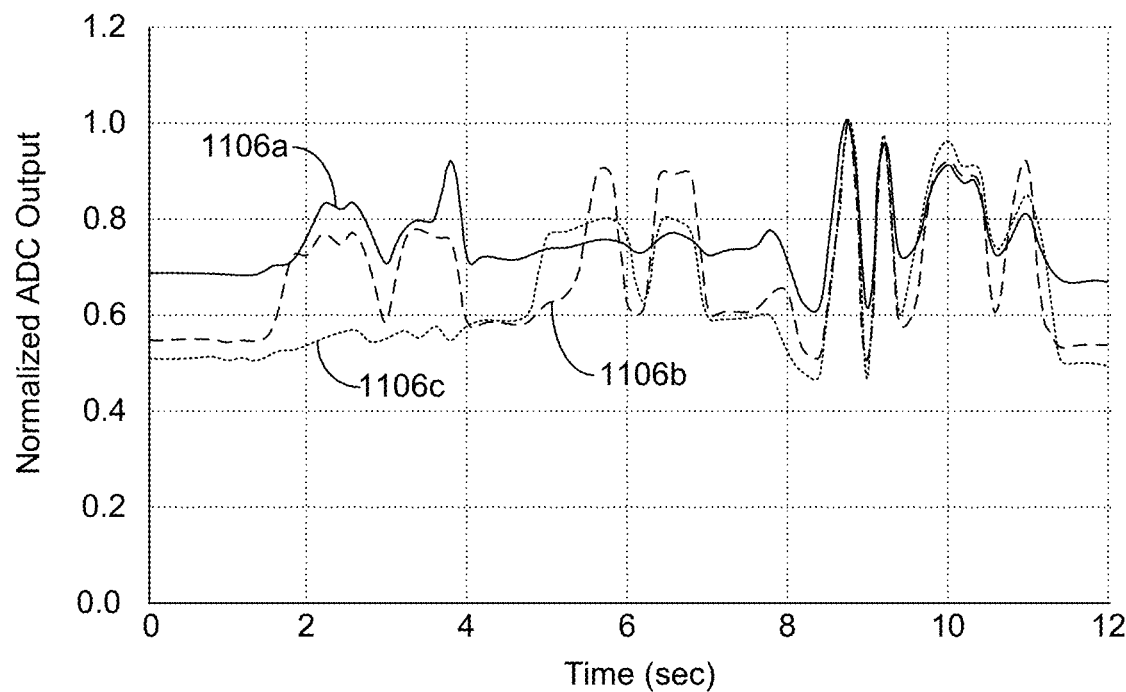

FIG. 11B depicts a continuous mode test result, where curve 1106a corresponds to the normalized ADC output of pressure sensor 609a, curve 1106b corresponds to the normalized ADC output of pressure sensor 609b, and curve 1106c corresponds to the normalized ADC output of pressure sensor 609c. Between 2 to 4 seconds, when the left side of the jaw clenches (episode 1), only pressure sensors 609a and 609b (curves 1106a and 1106b, respectively), which are in the proximity of the action, respond. Due to its remote location, pressure sensor 609c (curve 1106c) does not respond. Between 5 to 7 seconds, when the right side of the jaw clenches (episode 2), pressure sensors 609b and 609c (curves 1106b and 1106c, respectively) respond, whereas pressure sensor 609a (curve 1106a) does not respond.

Between 8 to 11 seconds, when all sides of the jaws clench (episode 3), the action elicits a response from all three sensors. It should be noted that in episode 3, the biting force from all sides of the jaws is greater than that in episodes 1 and 2 with either side of the jaw, which is reflected in the larger magnitude recorded on the y-axis. The sensing data from pressure sensors 609d and 609e were measured as well, but not plotted for clarity.

When bruxing occurs during sleep, intervention by a clinician or therapist may not be readily available. An external processing unit 106 such as, e.g., a smart phone module or a personal computer with its superior computing power can compare the bruxing activity over an extended period of time and initiate a response only when recorded stress data are inconsistent with restful sleep or indicate potentially damaging force to the teeth or muscles. Intervention measures include the microprocessor triggering a mild electrical pulse to alert the wearer of bruxing or activating a drug delivery system to release a therapeutic agent, each of which may be integrated into the mouth guard. For instance, a compact coin type vibration motor (B1034, Yuesui Inc.), which is popularly used for a mobile phone vibrator, may be included for a hardware-based intervention approach in SMS. When bruxing occurs, mild vibration can be initiated to disturb the bruxing activity to prevent further dental or tissue damage. The frequency of the vibratory intervention may be calibrated and customized to the user. The SMS may be highly customizable according to patient needs.

Other forms of intervention may include initiating music therapy and/or activating a wake-up alarm. Once a response has been triggered to initiate music therapy, the external processing unit 106 (e.g., cell phone or linked computer) can determine from the patient's bruxing data whether the therapy has been effective. When bruxing activity fails to decline following the intervention, the external processing unit 106 may determine whether to administer additional therapy or alert a clinician. For example, a message may be sent to the clinician, who may then make contact with the user in response to the message. Captured data may also be transmitted to allow the clinician to evaluate the current conditions of the user. In this way, the clinician may be able to (a) remotely monitor the efficacy and progress of the user's self-management of stress, (b) establish a database to record the time course of stress levels of user on, e.g., a clinic server, (c) provide a basis for deciding whether follow-up sessions in the clinic should be recommended, (d) remotely change the automated therapeutic protocol for further personalization, and/or (e) intervene in person, e.g., via a phone call, if necessary.

As discussed, the system interfaces wirelessly with an external processing unit 106 such as, e.g., a mobile device or PC. For example, Bluetooth may be used for communications between SMS and a cell phone. Bluetooth offers a relatively large coverage range (about 100 meters for Class A device), high data rate (up to 2.1 Mb/s) and noise immunity by frequency-hopping spread spectrum (FHSS) technique. The electronic processing circuitry 606 of the mouth guard can also include an integrated Bluetooth chip. In this way, a mobile smart phone may be used as the external processing unit 106 allowing for data acquisition device without a separate microprocessor or computer. An application operating on the cell (or smart) phone can control the activities of the SMS. For example, the application may store bruxing activity in the cell phone memory received from the mouth guard, analyze the bruxing activity by comparing the acquired data with preset threshold values, and/or initiate music therapy to improve relaxation if the threshold levels are exceeded. The collected data needs to be securely transferred through an encrypted or password protected channel.

The SMS may be used as a mHealth tool for chronic stress management. An external processing unit 106 such as, e.g., a smart phone, a smart watch (e.g., an Apple iWatch or Samsung Galaxy Gear), a PDA, a tablet (PC) device, a portable computer, or other mobile device may be used to continuously monitor health conditions for patients, realizing an "mHealth" (mobile health), a term used for the practice of medicine and public health supported by mobile devices. In some cases, applications such as, e.g., eMOCHA (electronic Mobile Open-source Comprehensive Health Application), can offer secure, highly flexible and adaptable mHealth app platforms, that may be utilized by the SMS with Android-supported devices. The curves of FIG. 11B demonstrate the ability of SMS to measure and quantify the intensity and duration of bruxism in real-time outside a research setting and for wirelessly transmitting data. The external processing unit 106 may execute appropriate applications (apps) to implement the mHealth monitoring system.

In some cases the mouth guard may be a retainer, which is a temporary device used to adjust and/or maintain alignment of teeth before and/or after dental braces. The integrated sensors can be used to monitor the use of the retainer by the wearer. For example, pressure and/or temperature sensors can be used to monitor how long the retainer has been worn and/or when the retainer can be removed based upon sensed force levels. Pressure and/or inertia sensors can also provide information regarding movement of the retainer while in use. The SMS can provide feedback to the wearer and/or others regarding use of the retainer.

Various examples are provided for smart mouth guards. In various aspects, among others, a diagnostic mouth guard is disclosed that includes a plurality of pressure sensors; and processing circuitry in communication with the plurality of pressure sensors, the processing circuitry configured to provide pressure sensor data to an external processing unit when located in an oral cavity. The processing circuitry can include an analog-to-digital converter (ADC), a microprocessor, and a transceiver embedded in the mouth guard. The transceiver can be configured to communicate with the external processing unit over a wireless channel. The diagnostic mouth guard can also include a temperature sensor, a pH sensor and/or an inertia sensor. The diagnostic mouth guard can also include an intervention feedback unit. The intervention feedback unit can include a vibration motor.

Various aspects of the present disclosure include a system comprising the diagnostic mouth guard and the external processing unit. In any one or more aspects of the system, the external processing unit can be configured to obtain the pressure sensor data from the processing circuitry of the diagnostic mouth guard. The external processing unit can be configured to process the obtained sensor data to determine a condition of bruxism. The external processing unit can be configured to initiate an intervention in response to the determination of the condition of bruxism. The intervention can be an initiation of music therapy and/or an initiation of feedback provided by the diagnostic mouth guard. The feedback provided by the diagnostic mouth guard can be a vibration. In any one or more aspects of the system, the external processing unit can be configured to provide an indication of the condition of bruxism through a graphical user interface (GUI).

In any one or more aspects of the system, the external processing unit can be a smart phone, a smart watch, a personal computer or a tablet computer. The smart phone, smart watch, personal computer or tablet computer can be configured to implement an "mHealth" (mobile-health) monitoring system. In any one or more aspects of the system, the external processing unit can be a cell phone configured to implement an "mHealth" (mobile-health) monitoring system, In any one or more aspects, the smart mouth guard can be a retainer.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A diagnostic mouth guard, comprising:
   a body for insertion into an oral cavity and placement over a plurality of adjacent teeth of a user, the body comprising a medial region that is disposed between upper and lower teeth of the user when the body is thus placed over the plurality of adjacent teeth;
   a plurality of pressure sensors mounted in the medial region of the body, each individual pressure sensor of the plurality of pressure sensors occupying a position in the body between the upper and lower teeth when the body is thus placed over the plurality of adjacent teeth and comprising an elastomeric member having on a first side thereof a corresponding first conductive pad and on a second side thereof a member selected from the group consisting of a second conductive pad, an electrical path to ground, and a combination thereof, the elastomeric member having a thickness and a Young's modulus selected and configured so that each individual pressure sensor constitutes a capacitive transducer having a capacitance correlating with a biting force applied to the medial region of the diagnostic mouth guard at a location of such individual pressure sensor on the elastomeric member; and
   processing circuitry, in communication with the plurality of pressure sensors, configured to provide pressure sensor data, based upon the capacitance of the individual pressure sensors, to an external processing unit when the diagnostic mouth guard is located in the oral cavity.

2. The diagnostic mouth guard of claim 1, wherein the processing circuitry includes an analog-to-digital converter (ADC), a microprocessor, and a transceiver embedded in the diagnostic mouth guard.

3. The diagnostic mouth guard of claim 2, wherein the transceiver is configured to communicate with the external processing unit over a wireless channel.

4. The diagnostic mouth guard of claim 1, further comprising a temperature sensor.

5. The diagnostic mouth guard of claim 1, further comprising an intervention feedback unit configured to provide feedback to the user of the diagnostic mouth guard when the diagnostic mouth guard is located in the oral cavity.

6. The diagnostic mouth guard of claim 5, wherein the intervention feedback unit comprises a vibration motor.

7. The diagnostic mouth guard of claim 1, further comprising an inertia sensor comprising an accelerometer or a gyroscope.

8. The diagnostic mouth guard of claim 1, comprising the external processing unit, in communication with the processing circuitry when the diagnostic mouth guard is located in the oral cavity, configured to process the pressure sensor data, and constituting the external processing unit of claim 1.

9. The diagnostic mouth guard of claim 8, wherein the external processing unit is configured to obtain the pressure sensor data from the processing circuitry of the diagnostic mouth guard.

10. The diagnostic mouth guard of claim 9, wherein the external processing unit is configured to process the obtained sensor data to determine a condition of bruxism.

11. The diagnostic mouth guard of claim 10, wherein the external processing unit is configured to initiate an intervention in response to the determination of the condition of bruxism.

12. The diagnostic mouth guard of claim 11, wherein the intervention is an initiation of music therapy.

13. The diagnostic mouth guard of claim 11, wherein the intervention is an initiation of feedback provided by the diagnostic mouth guard.

14. The diagnostic mouth guard of claim 13, wherein the feedback provided by the diagnostic mouth guard is a vibration.

15. The diagnostic mouth guard of claim 10, wherein the external processing unit is further configured to provide an indication of the condition of bruxism through a graphical user interface (GUI).

16. The diagnostic mouth guard of claim 8, wherein the external processing unit is a smart phone or a smart watch.

17. The diagnostic mouth guard of claim 8, wherein the external processing unit is a personal computer.

18. The diagnostic mouth guard of claim 8, wherein the external processing unit is a tablet computer.

19. The diagnostic mouth guard of claim 18, wherein the tablet computer is configured to implement an "mHealth" (mobile-health) monitoring system.

20. The diagnostic mouth guard of claim 8, wherein the external processing unit is a cell phone or a smart watch configured to implement an "mHealth" (mobile-health) monitoring system.

21. The diagnostic mouth guard of claim 1, wherein the individual pressure sensors comprise an elastomer disposed between an electrode and a portion of the plurality of adjacent teeth of the user.

* * * * *